United States Patent [19]

Kramann et al.

[11] 4,043,345

[45] Aug. 23, 1977

[54] CATHETER

[75] Inventors: Bernhard Kramann, Planegg; Heinrich Tammen, Munich, both of Germany

[73] Assignee: Byk Gulden Lomberg Chemische Fabrik GmbH, Constance, Germany

[21] Appl. No.: 571,984

[22] Filed: Apr. 28, 1975

[30] Foreign Application Priority Data

May 2, 1974 Germany ............................ 2421294

[51] Int. Cl.² ........................................... A61M 25/00
[52] U.S. Cl. ................................. 128/349 R; 128/262
[58] Field of Search ............................ 128/348–351, 128/262; 137/525; 251/342; 222/526–529

[56] References Cited

U.S. PATENT DOCUMENTS

| 3,502,069 | 3/1970 | Silverman | 128/2 M |
| 3,506,011 | 4/1970 | Silverman | 128/348 |
| 3,802,461 | 4/1974 | Witt | 137/525 |
| 3,911,927 | 10/1975 | Rich et al. | 128/262 |

FOREIGN PATENT DOCUMENTS

| 588,679 | 2/1925 | France | 273/65 D |
| 454,642 | 7/1928 | Germany | 128/262 |

*Primary Examiner*—Dalton L. Truluck
*Attorney, Agent, or Firm*—Toren, McGeady and Stanger

[57] ABSTRACT

A catheter including a flexible hose attached to one end of a rigid tube through which fluid pressure may be applied to invert said hose from an invaginated position within said tube to an exserted position extending outwardly of said tube has formed at the distal of said hose a valve which remains closed when the hose is in the invaginated position and which opens with the hose in its exserted position. The valve is formed integrally by portion of the hose distal end by cutting the distal end along a plane extending obliquely of the axis of the hose and forming the distal end walls of the hose in an abutting configuration defining therebetween an orifice which tends to remain closed by abutment of the distal end walls against each other when the hose is in its invaginated position, and particularly when fluid pressure is applied within the tube, with the abutting wall portions between which said orifice is defined tending to separate to open the orifice when the hose is exserted from the tube.

12 Claims, 18 Drawing Figures

CATHETER

BACKGROUND OF THE INVENTION

The present invention relates generally to a catheter and more particularly to a bladder catheter. Generally, the invention relates to the type of catheter which is constructed to include a tube through which fluid pressure may be applied and a resilient hose which is usually invaginated into the interior of the tube and which is adapted to be exserted therefrom by the action of fluid pressure within the tube.

It has been previously proposed to line body cavities such as, for example, the urethra by means of a lining member which may be exserted or caused to protrude by application thereto of a pressure medium in order to enable introduction of instruments such as a catheter into a body cavity lined in this fashion, with the catheter being inserted subsequently or at the same time as the exsertion of the lining member. In this regard, reference is made, for example, to U.S. Pat. No. 3,589,356 and to German patent specification (Offenlegungsschrift) 2,021,634.

Catheters, which are introduced into the body in accordance with this principle, are particularly suited for use upon female patients when it is necessary to remove urine from the bladder and when medication in liquid form must be dispensed. An advantage arises in the use of such instruments in that sliding movement within the urethra is avoided thereby effectively avoiding the possibility of infective material present in the urethra becoming entrained into the bladder. This advantage arises due to the exsertion of the lining member or hose effected by the application of fluid pressure when the catheter is to be introduced into the bladder. As a result, the likelihood of bladder infection is reduced or eliminated.

However, it has been found that the practical application of the aforementioned type of catheterization may involve complications and may not be capable of performance without danger. Owing to the substantial friction which may occur between the hose which is being exserted and the tube of the instrument, there occurs a danger that the operator may lose his sense of feel for the restricted passages and curves in the urethra thereby giving rise to the possibility that injury may occur.

The present invention is intended to provide improvements over the previously proposed type of catheter wherein a flexible hose invaginated into a generally rigid tube may be exserted therefrom by the action of fluid pressure in such a manner that catheterization may be performed substantially without danged to a patient and in a substantially simpler manner while at the same time reducing the structural complexity of the device.

SUMMARY OF THE INVENTION

Briefly, the catheter of the present invention may be described as including a substantially flexible hose which is attached or integrally formed with one end of a generally rigid tube, with the hose having configured to form at its distal end, valve means which is adapted to open when the hose is exserted from the tube but which remains closed when the hose is invaginated within the tube. At the end of the tube opposite the end having the hose connected thereto, connection may be made to a spigot of a piston-type syringe in order to introduce fluid pressure into the tube and thereby effect exsertion of the hose.

The valve means formed at the distal end of the hose is essentially comprised of parts of the hose wall itself which are formed to define orifice means through the hose wall and which are folded or arranged in abutting relationship so as to close the orifice means when the hose is invaginated and to open the orifice means when the hose is exserted. Due to the construction of the distal end of the tube forming the value or orifice means, the abutting wals forming the valve means tends to be urged together to maintain the orifice means defined therebetween closed by the pressure which is introduced into the tube in order to exsert the hose from the tube.

In one aspect of the invention, the means is formed by first inverting or turning the hose inside out after it has been manufactured. The hose is constructed as a generally open-ended cylindrical member. A cut is made at the distal end of the inverted hose along a plane which extends oliquely to the central axis of the hose. As a result, the distal end of the inverted hose is formed with one side longer than the other, i.e., with a generally oblong annular end wall surrounding the distal open end of the hose. By folding the longer side of the hose into a reentrant S-shaped configuration, the opposite sides of the hose wall may be brought into abutting relationship with the folded longer hose side pressing against the shorter hose side. Thus, the distal open end of the hose will be closed. When the hose is again inverted or turned inside-out by being exserted from the tube, the distal end walls unfold to open the means of the catheter.

In another aspect of the invention, the orifice means at the distal end may be formed by first forming the hose with a completely closed distal end which is indented when the hose is in its inverted or inside-out position. With the distal end closed and indented, a generally reentrant hose end will be formed with the walls of the hose extending about the distal end being in an overlapping arrangement. By cutting the hose along a plane extending obliquely to the hose axis on one side only by the distal end, an opening is formed between the end walls of the hose which, when the hose is inverted or invaginated, will be in abutment to maintain the opening in a closed condition. Again, by reversing the inverted position of the hose, as would occur when the hose is exserted from the tube, the overlapping walls forming the valve means will separate thereby opening the orifice means.

The proximal end of the hose is attached to the tube either by being formed integrally therewith or by attachment means which may include a groove, ridge, or the like formed in the end of the tube with the hose being positioned about the tube end over the groove and secured thereat by a cuff, internal peripheral rib or spring ring or the like which holds the hose upon the tube end. The tube is constructed as a rigid or semi-rigid body and may be formed of plastic material, metal, glass or the like with plastic being the preferred material.

Because of the features of the invention, it is not only possible to achieve the aim of the invention in a convenient manner but it is also possible to produce a catheter wherein the hose simultaneously serves as a bladder catheter. Furthermore, owing to the resulting economic production techniques which can be utilized in manufacturing the catheter, the entire device may be discarded after one use thereof. Additionally, it is possible for preferential use to be made of catheterization by means of a hose which is exserted, because the introduction of the catheter is substantially more pleasant for most of the various types of investigations which must be performed and troublesome complications occurring after catheterization, such as smarting pain or emptying of the bladder, no longer occur. Because of the simple construction of the device of the invention, and its easy application, the new exsertable catheter may also be used without danger by nursing personnel.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
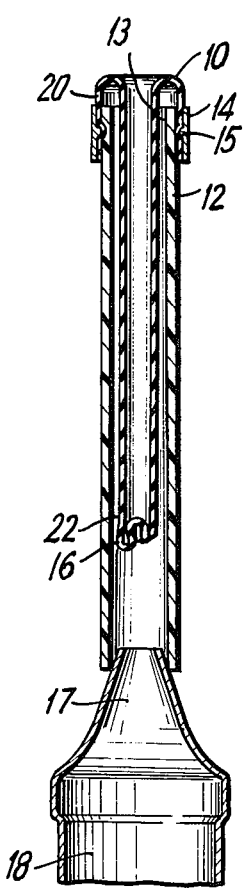
FIG. 1 is a longitudinal sectional view of the catheter of the present invention showing the hose invaginated within the tube.
Figure 2:
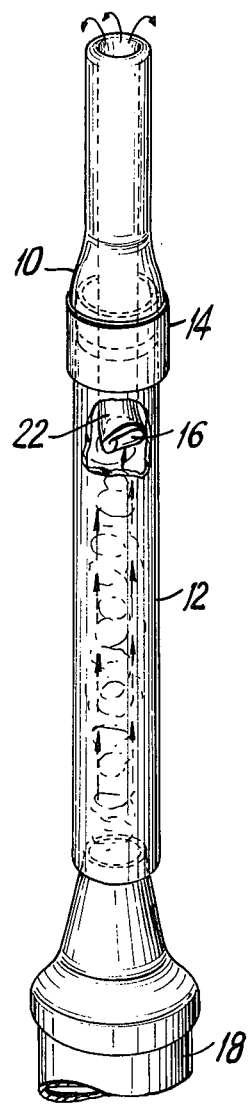
FIG. 2 is a longitudinal perspective view showing the hose in the process of being exserted.
Figure 3:
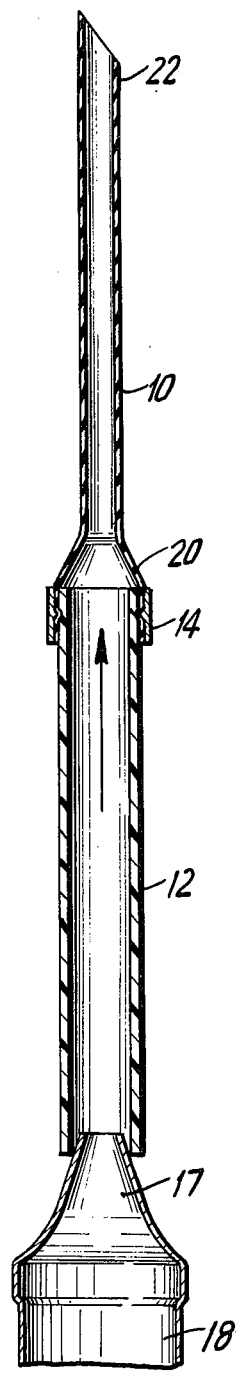
FIG. 3 is a longitudinal sectional view showing the catheter with the hose fully exserted.

Referring now to FIGS. 1, 2 and 3 of the drawings, the catheter assembly of the present invention is shown as basically comprising a hose 10 attached to one end of the tube 12. The hose 10 is formed as a resilient body and may be made of a silicone compound or other suitable material such as, for example, latex or rubber. The tube 12 is generally rigid and may be manufactured of any suitable material, preferably a plastic material.

The hose 10 comprises a proximal end 20 attached to one end of the tube 12 and a distal end 22. The end of the tube 12 having the hose 10 attached thereto is formed with a groove or ridge 13. In attaching the proximal end 20 to the tube 12, the hose is drawn over the outside of the tube and a cuff 14 or other suitable connecting member is fitted to extend about the proximal end of the hose 10. The cuff 14 may be formed with an inner peripheral rib 15 configured to be mated with the groove 13 in order to provide a secure connection between the hose 10 and the tube 12. The cuff 14 may be made of elastic or resilient material in order to provide a spring force holding the hose 10 upon the tube 12.

The distal end 22 of the hose 10 is shaped to form therein integral valve means 16, to be more fully described hereinafter. In the position shown in FIG. 1, the hose 10 is invaginated within the tube 12 with the hose being in an inverse position or turned inside out. The end of the tube 12 opposite the end connected to the hose 10 is in engagement with a piston-type syringe 18 having a spigot 17. The syringe 18 operates to introduce fluid pressure into the tube 12. As depicted in Fig. 2, as the fluid pressure enters the tube 12, it tends to push the hose 10 outwardly thereof thereby to exsert the hose from within the tube. The valve means 16 formed at the distal end 22 of the hose 10 remains closed while the hose 10 is being exserted by the fluid pressure within the tube 12. In FIG. 3 the hose 10 is shown in its fully exserted position. When the tube 10 is fully exserted, the valve 16 opens.

Because of the invagination of the hose 10 within the tube 12 as shown in FIG. 1, and due to the fact that the hose is thereby turned inside out, the hose material becomes softer and more pliant than when it is in its original condition. Furthermore, the protrusion or exsertion of the catheter hose whereby it is brought from the position shown in FIG. 1 into the position shown in FIG. 3 can be facilitated by effecting measures discussed hereinafter which will operate, as well, to reduce the fluid pressure which must be applied in the operation of the catheter. These measures include the following:

a. The hose 10 is preferably constructed with a conical configuration whereby its external diameter decreases from the proximal end 20 to the distal end 22 with the portion of the hose forming the valve means 16 being retained with an approximately constant diameter.

b. The wall thickness of the hose 10 is preferably arranged to vary along its length by progressively decreasing from the proximal end 20 the the distal end 22.

c. In the position shown in FIG. 1 the hose 10 is inverted or turned inside out whereby its outer surface becomes its inner surface. As a result, upon protrusion or exsertion of the hose 10 from the tube 12, the hose becomes once again reversed so that its outer side as originally formed becomes, once again, the outer side of the catheter hose.

The piston-type syringe 18 may be of the throw-away type and in order to effect exsertion of the hose the syringe is generally filled with a sterile sodium chloride solution or sterile distilled water. If the filled piston syringe is applied to the free end of the tube 12, even in a case where a small piston pressure is applied, the hose 10 will be caused to protrude out of the tube 12 with the pressure thus provided continuing to be applied so that the protrusion of the hose 10 continues until the hose extends through the urethra and enters the bladder. At this point, the valve means 16 is opened and the sealing action thereof ceases. With the valve 16 in the opened condition within the bladder, the spigot 17 may be detached from the tube 12. In a case where a syringe which is permanently connected to the tube 12 is used, the piston of the syringe may be withdrawn, for example, for the purpose of removing urine.

Figure 4:
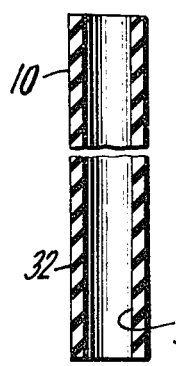
FIG. 4 is a sectional view of the hose as initially formed.
Figure 5:
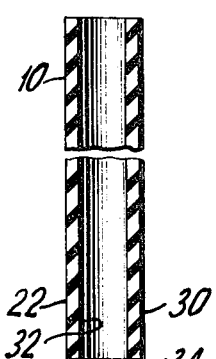
FIG. 5 is a sectional view showing the hose of FIG. 4 inverted or turned inside out.
Figure 6:
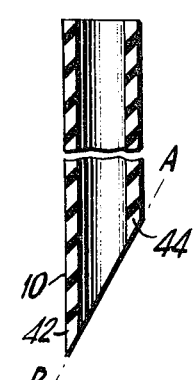
FIG. 6 is a sectional view showing the hose cut at its end along an oblique plane.
Figure 7:
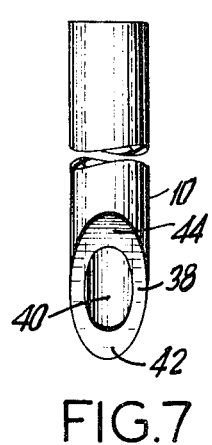
FIG. 7 is a side view of the hose of FIG. 6.

The valve means 16 may be formed at the distal end 22 of the hose 10 in several ways. Referring now to FIG. 4, a hose 10 in its original condition is shown as comprising a generally cylindrical tubular configuration having an inner wall 30 and an outer wall 32. In the manufacture of the device, the hose 10 is inverted or turned inside-out as shown in FIG. 5 so that its originally inner surface 30 now becomes its outer surface while its originally outer surface 32 now becomes its inner surface. Subsequently, the distal end of the hose switch, as shown in FIG. 5, comprises a generally circular annular wall 34 surrounding and defining a generally circular orifice 36, is cut along a plane A-B in order to form the distal end of the hose 10 with a generally oblong configuration, best seen in FIG. 6, and FIG. 7 with an annular end wall 38 extending obliquely to the central axis of the tube 10 being formed to surround and define orifice means in the form of a generally oblong orifice 40. With the hose 10 in this condition, it will be seen that one side 42 of the hose will be longer than the opposite side 44 thereof.

Figure 8:
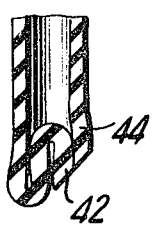
FIG. 8 is a partial sectional view showing the valve means formed at an end of the hose.

The longer side 42 of the hose 10 is then folded or tucked into the interior of the hose 10, as shown in FIG. 8 so that the end of the long side 42 will be in abutment with the end of the short side 44. As a result, the side 42 will assume a generally reentrant S-shaped configuration depicted in FIG. 8. The sides 42 and 44 will define therebetween the orifice 40 but because sides 42 and 44 are in abutting relationship, held together by the spring force created as a result of the formation of the side 42 in its S-shaped arrangement, a spring force will be created closing the orifice 40.

Figure 9:
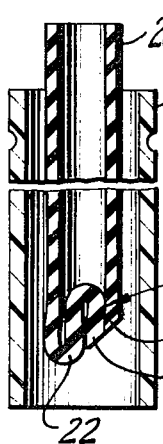
FIG. 9 is a sectional view illustrating the manner in which the hose may be inserted into the tube.
Figure 10:
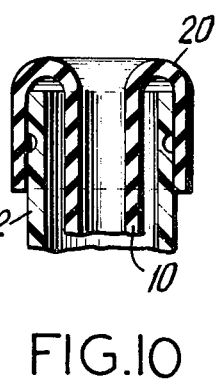
FIG. 10 is a partial sectional view showing the manner whereby the hose may be attached to the tube.

After insertion of the side 42 into the inserter of the hose 10, the hose is placed while in its inverted position within the tube 12, as shown in FIG. 9. The distal end of the hose 22 comprising the valve means 16 formed by the abutting side walls 42 and 44 is first introduced into the tube 12 and the proximal end 20 of the hose 10 is folded over the end of the tube 12, as shown in FIG. 10. With the hose 10 in the position shown in FIG. 10, the proximal end 20 may now be connected to the end of the tube 12 to form the attachment depicted in FIG. 1. After connection of the proximal end 20 to the tube 12, the catheter assembly will be configured essentially as shown in FIG. 1 with the hose 10 invaginated within the tube 12.

Figure 11:
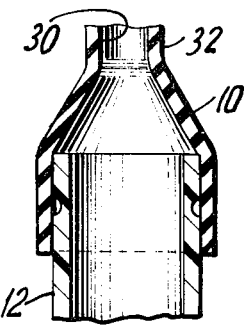
FIG. 11 is a partial sectional view showing another mode for attaching the hose to the tube.

In another aspect of the invention, the procedure for assembling the hose 10 and the tube 12, and for forming the valve means 16 may be performed by first placing the hose 10 over the tube 12 in the position shown in FIG. 11 with the hose 10 in its original condition, that is, with its outer surface 32 on the exterior of the hose and with the inner surface 30 on the interior thereof. Thus, the hose 10 is first placed over the tube 12 without performing the step of inverting the hose or turning it inside-out.

Figure 12:
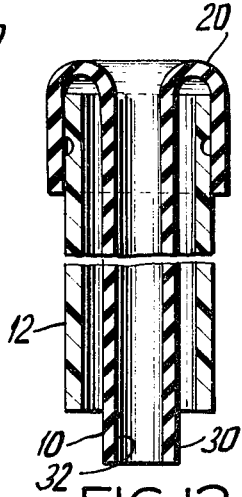
FIG. 12 shows the hose invaginated into the tube after it has been attached thereto in the manner shown in FIG. 11.
Figure 13:
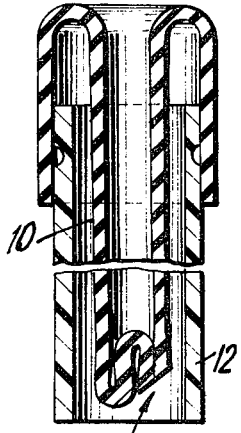
FIG. 13 shows the invaginated hose with the valve means formed at one end thereof.

Subsequently, the hose is inverted, as shown in FIG. 12, to invaginate the hose 10 within the tube 12 while the proximal end 20 of the hose 10 assumes a position overlapping the end of the tube 12. As shown in FIG. 12, the hose 10 is made somewhat longer than the tube 12 so that it will protrude from the bottom open end thereof. With the hose 10 in this position, the valve means 16 may be formed in the manner described previously with reference to FIGS. 5, 6, 7 and 8. Subsequently, the hose 10 is raised upwardly into the position shown in FIG. 13 so that the vavle means 16 will lie within the interior of the tube 12 with the hose 10 in its invaginated or reversed position.

Figure 14:
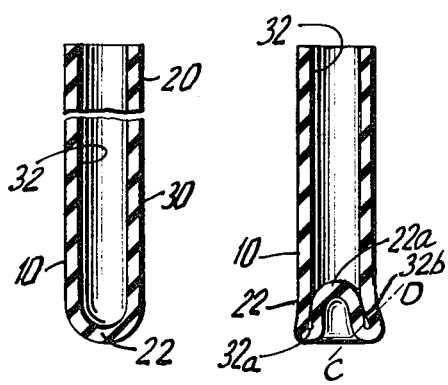
FIG. 14 is a sectional view showing a hose used in another embodiment of the invention.

By another aspect of the invention, the valve means 16 may be formed by a somewhat different method. Referring to FIG. 14, the hose 10 may be formed as a generally cylindrical body with its proximal end 20 open and with its distal end 22 closed. In the condition shown in FIG. 14, the hose 10 has already been inverted or turned inside out so that its originally inner side 30 is now its outer side whereas its originally outer side 32 is now its inner side.

Figure 15:
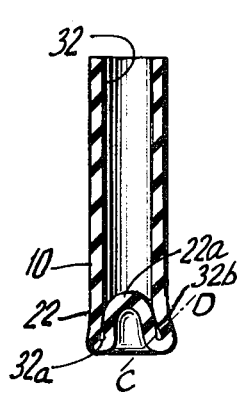
FIG. 15 is a partial sectional view showing the hose of FIG. 14 during the formation of the orifice means therein.

Subsequently, the closed distal end 22 is indented or made reentrant into the body of the hose 10, as shown in FIG. 15. As a result, a reentrant or indented portion 22a will be formed. The distal end 22 will now be arranged with portions of the side wall 32 of the hose in an overlapped arrangement as indicated at 32a and 32b. Subsequently, the hose is cut along one side thereof along a plane C-D which extends obliquely to the central axis of the hose 10. As a result, an orifice constituting the orifice means of the invention will be formed between the overlapped wall portions indicated at 32b, but because of the shape of the indented portion 22a, this orifice will be maintained closed due to the abutting relationship of the portions of the wall 32 across which the cut is taken. As a result, it will be apparent that, after the cut is made across the plane C-D, valve means 16 will be formed generally similar in configuration to the valve means previously depicted, for example, in FIG. 8.

Of course, it will be apparent that the proximal end of the hose 20 may be connected to the tube 12, and the valve means 16 may be formed, by any one of the techniques previously described, for example, with reference to FIG. 10 or FIGS. 11-13.

Figure 16:
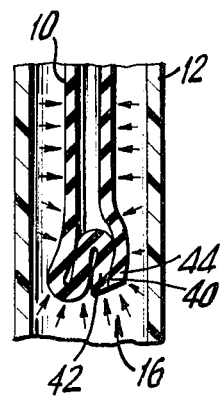
FIGS. 16 and 17 are partial sectional views illustrating the manner whereby fluid pressure within the tube acts upon the invaginated hose particularly at the end thereof having the valve means.
Figure 17:
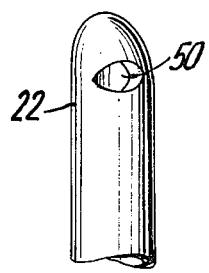

FIGS. 16 and 17 depict the action of the fluid pressure internally of the tube 12 against the valve means 16. As shown by the arrows in FIG. 16, the pressure is exerted so that the direction of the forces created tend to maintain the valve means 16 closed. That is, assuming that the embodiment depicted in FIG. 16 is similar to the embodiment depicted in FIG. 8, the ends 42 and 44 will be urged together to close the orifice 40 by the action of the internal fluid pressure as well as by the spring force created as a result of the S-shaped configuration of the end 42. However, the internal fluid pressure will act in a direction to exsert the hose 10 outwardly of the tube 12, as depicted in FIG. 17 while at the same time tending to maintain the valve means 16 closed. When the hose 10 is in its fully exserted or extended position depicted in FIG. 3, the ends 42 and 44 will be reversed thereby opening the orifice 40 as the ends 42 and 44 are relieved of the pressure tending to maintain them in abutting relationship.

Figure 18:
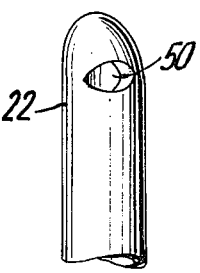
FIG. 18 is a perspective view showing the end of the hose in its exserted extended position with the orifice means opened.

FIG. 18 shows the distal end 22 of the tube in its fully extended position, and if the valve means is formed by the method described with reference to FIGS. 14 and 15, a lateral port or orifice 50 will be opened.

Accordingly, it will be seen that in any of the embodiments of the present invention, the valve means 16 will be maintained closed during exsertion of the hose 10 by the spring tension of the inverted hose. Additionally, the pressure of the propulsion medium supports the closed position of the valve as indicated by the arrows in FIG. 16. Of course, it is to be understood that the fluid medium which is utilized may be gaseous or liquid and that accordingly the device may utilize pneumatic or hydraulic pressure to effect exsertion of the hose. When the hose is completely exserted, the valve means 16 automatically opens. It will be apparent that the valve means are formed integrally with the hose 10 and solely from the material from which the hose is formed. Thus, there is no need for auxiliary means such as springs or other separate elements. As a result of the present invention, it is possible to manufacture a catheter in a simple manner with the valve means being formed from portions of the structure integral therewith. The valve may be constructed along different lines, it being important only that upon protrusion or exsertion the distal end of the hose having the valve means formed thereat operates to automatically open the valve means.

While specific embodiments of the invention have been shown and described in detail to illustrate the application of the inventive principles, it will be understood that the invention may be embodied otherwise without departing from such principles.

What is claimed is:

1. A catheter comprising a substantially rigid tube adapted to have fluid pressure introduced through one end thereof, a hose having a proximal end in fluid-tight engagement with the other end of said tube and a distal end, said hose being invaginated within said rigid tube, said hose being structured to be brought from an invaginated position into the exserted position by introduction of fluid pressure through said one end of said tube, and orifice means defined through wall portions of said hose at said distal end thereof, said wall portions having said orifice means defined therethrough being arranged in an overlapping abutting configuration to provide means creating a force to maintain said orifice means closed by maintaining said wall portions in said abutting relationship when said hose is in said invaginated position, said wall portions being configured to separate to release said abutting relationship thereby to open said orifice means when said hose is brought to said exerted position.

2. A catheter according to claim 1 wherein the position of said wall portions becomes inverted when said wall portions move from said abutting relationship and separate from each other to open said orifice means.

3. A catheter according to claim 1 wherein said wall portions are configured to have fluid pressure within said tube act thereupon to tend to retain said orifice means closed when said hose is in said invaginated position.

4. A catheter according to claim 1 wherein said abutting wall portions of said hose comprise a pair of opposed walls with one of said walls being arranged in an S-shaped configuration.

5. A catheter according to claim 1 including a piston member operatively connected with said one end of said tube for introducing hydraulic pressure therethrough.

6. A catheter according to claim 1 wherein said hose is structured to form a generally elongated tubular configuration having a central longitudinal axis, said wall portions being formed to include an annular end wall located at said distal end of said hose defining said orifice means thereat, said annular end wall lying in a plane extending obliquely to said longitudinal axis.

7. A catheter according to claim 1 wherein said distal end of said hose is shaped to assume a generally reentrant indented configuration when said hose is in said invaginated position thereby to form the walls of said hose at said distal end in an overlapping arrangement, said distal end having an oblique outer wall defining said orifice means through said distal end, said oblique outer wall extending on one side only of said hose and forming the terminal portions of said overlapping walls.

8. A catheter according to claim 1 wherein the other end of said tube having said hose connected thereto is formed with an outer circumferential groove, and wherein said hose is connected to overlap said groove, said catheter further including a cuff surrounding said hose with a spring force to hold said hose on said tube over said groove, said cuff being formed with an inner peripheral rib configured to mate with said groove.

9. A catheter according to claim 1 wherein said hose and said tube are integrally formed.

10. A catheter according to claim 1 wherein said tube is formed of plastic material.

11. A catheter according to claim 1 wherein said hose is formed with a diameter which progressively decreases from said proximal end towards said distal end.

12. A catheter according to claim 1 wherein said hose comprises a wall structure which progressively decreases in thickness from said proximal end toward said distal end.

* * * * *